United States Patent [19]

Matsui et al.

[11] Patent Number: 4,569,912
[45] Date of Patent: Feb. 11, 1986

[54] PRODUCTION OF BILIRUBIN OXIDASE

[75] Inventors: Susumu Matsui, Ootsu; Takako T. Sato, Ibaraki; Kazuo Nakajima, Kyoto, all of Japan

[73] Assignee: Takara Shuzo Co., Ltd., Kyoto, Japan

[21] Appl. No.: 570,027

[22] Filed: Jan. 11, 1984

[30] Foreign Application Priority Data

Jan. 25, 1983 [JP] Japan ................................. 58-10149

[51] Int. Cl.[4] .......................... C12N 9/02; C12R 1/645
[52] U.S. Cl. ..................................... 435/189; 435/911
[58] Field of Search ............................... 435/189, 191

[56] References Cited

FOREIGN PATENT DOCUMENTS 57-159487 10/1982 Japan .................................. 435/189

OTHER PUBLICATIONS

American Type Culture Collection Catalogue of Strains, 15th Edition, 1982, pp. 493, 494.

Primary Examiner—Lionel M. Shapiro
Attorney, Agent, or Firm—Wenderoth, Lind & Ponack

[57] ABSTRACT

Method for producing bilirubin oxidase by cultivating Schizophyllum commune K-17.

1 Claim, 7 Drawing Figures

— Before reaction
----- After reaction

→ After reaction
→ Before reaction
→ Authentic, Biliverdine
→ Authentic, Bilirubin — Before reaction
----- After reaction

PRODUCTION OF BILIRUBIN OXIDASE

The present invention relates to a method for producing bilirubin oxidase by the cultivation of a strain belonging to the genus Schizophyllum of the class Basidiomycetes.

Bilirubin is a yellow substance produced in the blood by degradation of hemoglobin. Rapid and accurate detection of bilirubin in serum is very important to medical diagnosis of the condition of diseases of human beings (for example, jaundice). With jaundice patients, bilirubin in serum increase abnormally, so that the degree of jaundice can be diagnosed by the measurement of bilirubin in serum.

Bilirubin oxidase was first reported by R. Brodersen and P. Bortels, and bilirubin was oxidized into biliverdine by insoluble bilirubin oxidase isolated from the brain of guinea pig [European Journal of Biochemistry, Vol. 10, 468 (1969)]. In recent years, however, it was reported that *Myrothecium verrucaria* MT-1 strain was found to produce bilirubin oxidase, and that the purified enzyme obtained from the culture filtrate oxidized bilirubin into biliverdine [Agricultural and Biological Chemistry, Vol. 45, 2385 (1981)].

In the analysis of specimens other than bilirubin in serum, bilirubin oxidase is also useful to remove bilirubin causing an error in measurement. That is, for the measurement of glucose or cholesterol in serum, a colorimetric method in which glucose oxidase or cholesterol oxidase is reacted with serum and the formed hydrogen peroxide is caught by peroxidase, is most popularly employed as a routine inspection method. Particularly, a development method with 4-aminoantipyrine and phenol has come to be a leading part of the enzymatic method, in terms of its simplicity and rapidity as well as stability of the reagent. This colorimetric method includes the measurement of formed red quinone dyes at 500 nm, but the presence of bilirubin in serum causes a negative error. Consequently, by reacting bilirubin oxidase with serum in advance to remove bilirubin, and then reacting glucose oxidase or cholesterol oxidase with the serum, a correct glucose value or cholesterol value of serum can be obtained.

The present inventors extensively studied bilirubin oxidase produced by a strain belonging to the class Basidiomycetes other than the above-mentioned bilirubin oxidase-producing microorganisms, and found that a certain kind of strain belong to the class Basidiomycetes produces a strong bilirubin oxidase in a culture liquor.

The strain used in the present invention is one belonging to the genus Schizophyllum of the class Basidiomycetes, for example *Schizophyllum commune* K-17. This strain was isolated from the fruit bodies growing in clusters on dead trees in Iwakura of Kyoto City, Japan.

The characteristics of the fruit body and spore of this strain are as follows:

Cap: 10–30 mm in diameter; densely covered with coarse hairs on the surface to assume a white, gray, flesh or brown color. Gills: white, gray or pale flesh color; longitudinally split at the margin, the split parts seeming to overlap each other. Flesh: leathery and tough; shrinks when dried but returns to the original shape when wetted. Spore: smooth, white in mass; takes a cylindrical form of 4–6×1.5–2μ. On comparing the above characteristics with the description in: Seiya Ito: Mycological flora of Japan, Vol. 2, No. 5, 1955 (published by Yoken-do, Tokyo, Japan) and Rokuya Imazeki and Tsugio Hongo: Colored Illustrations of Fungi of Japan, Vols. 1 and 2, it is apparent that this strain differs from the known strains of *Schizophyllum commune*, and has therefore been named *Schizophyllum commune* K-17. This strain was deposited at Fermentation Research Institute, Agency of Industrial Science and Technology, Japan under FERM BP-306 on May 17, 1982. This strain has an ability to form bilirubin oxidase.

The present invention will be explained in more detail as follows by referring partly to the accompanying drawings wherein.

In the cultivation of the microorganism to be used in this invention any well known nutrient source may be added to the culture medium, if it can be utilized by the strain used. As the carbon source, for example glycerol, glucose, starch, sucrose, maltose, lactose, dextrin, oils and fats, molasses and the like may be used. As the nitrogen source, yeast extract, peptone, corn steep liquor, defatted soybean, soybean powder, meat extract and the like are suitable. Also, inorganic substances and metallic salts such as phosphates, potassium salts, magnesium salts, iron salts, zinc salts and the like may also be added, and further vitamins and growth promotors may also be added.

In the cultivation of the strain belonging to the class Basidiomycetes, the amount of bilirubin oxidase to be produced varies largely depending upon the culture conditions. Generally, the culture temperature is preferably 20° to 35° C., the pH of the culture medium is preferably 4 to 7, and the production of bilirubin oxidase reaches maximum by aeration/stirring culture for 3 to 10 days. In this case, it is natural that the culture conditions should be determined so as to obtain a maximum output of bilirubin oxidase according to strains and compositions of culture medium employed.

Bilirubin oxidase produced by the strain of the present invention is present in the culture filtrate, and it may be separated as precipitate by adding 50 to 80 v/v % of an organic solvent (e.g. alcohol, acetone) or 20 to 80 w/v % of a precipitating agent (e.g. ammonium sulfate, calcium chloride) to the culture filtrate. The precipitate obtained is desalted by dialysis or Sephadex treatment to obtain a crude enzyme solution. For purifying the crude enzyme solution, gel filtration of the solution may be carried out on a column of Sephadex G-75 previously buffered with 0.1M phosphate buffer (pH, 7.0) to collect an active fraction. Thereafter, the active fraction is adsorbed to a column of DEAE-Sephadex A-50 previously buffered with 0.1M phosphate buffer (pH, 7.0), and the adsorbed matter is then eluted with 0.3M phosphate buffer (pH, 7.0) to collect an active fraction. This active fraction is then dialyzed against 0.01M phosphate buffer (pH, 7.0), and the internal solvent of dialysis is concentrated with a collodion membrane and lyophilized to obtain a purified enzyme powder.

The characteristic properties of bilirubin oxidase obtained by the present invention are as follows:

(1) Action

When the enzyme of the present invention acts on bilirubin, biliverdine is formed, and also, it oxidizes biliverdine into an unknown pale violet substance. That is, it catalyzes the following two-step reaction:

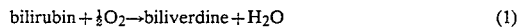

bilirubin + ½O$_2$ → biliverdine + H$_2$O  (1)

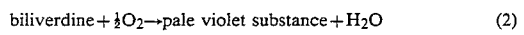

biliverdine + ½O$_2$ → pale violet substance + H$_2$O  (2)

(2) Optimum pH and pH stability

Figure 1:
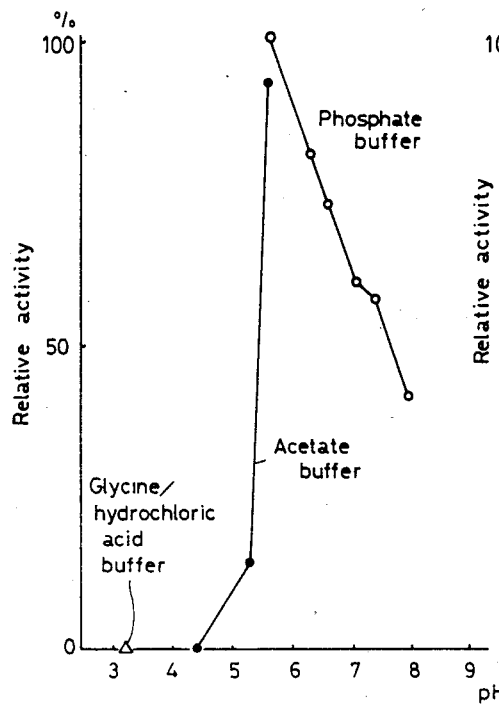
FIG. 1 shows a relation between the pH and activity of bilirubin oxidase obtained by the present invention.
Figure 3:
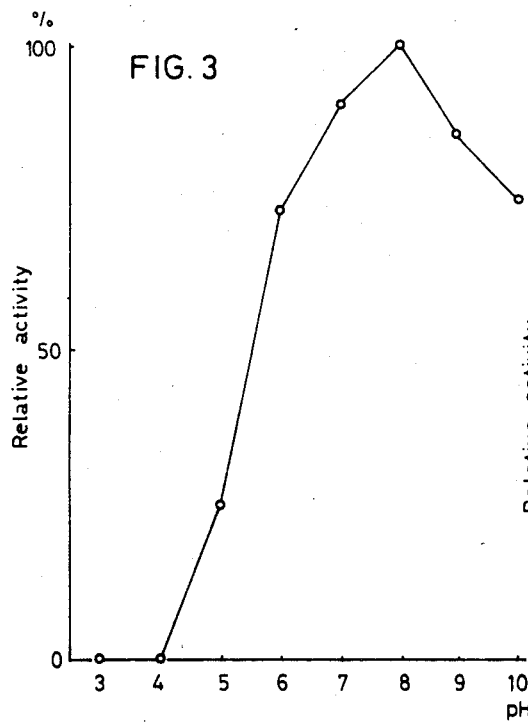
FIG. 3 shows a relation between the pH and activity after treating bilirubin oxidase at 4° C. and at varying pH values for 7 days.

An optimum pH for the present enzyme is in the vicinity of 5.5 to 6.0, showing an extremely high activity as shown by the curve in FIG. 1. The pH stability of the present enzyme when it was treated at 4° C. and at varying pH values for 7 days, is shown in FIG. 3. As is apparent from FIG. 3, the present enzyme is stable at a pH of 8.

(3) Optimum temperature and thermostability

Figure 2:
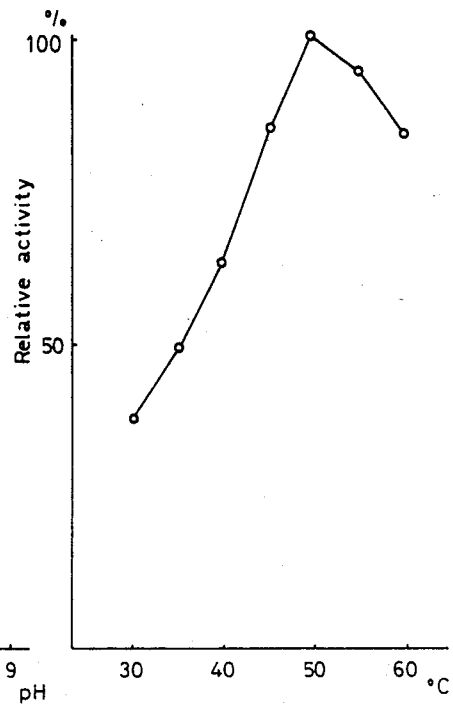
FIG. 2 shows a relation between the temperature and activity.
Figure 4:
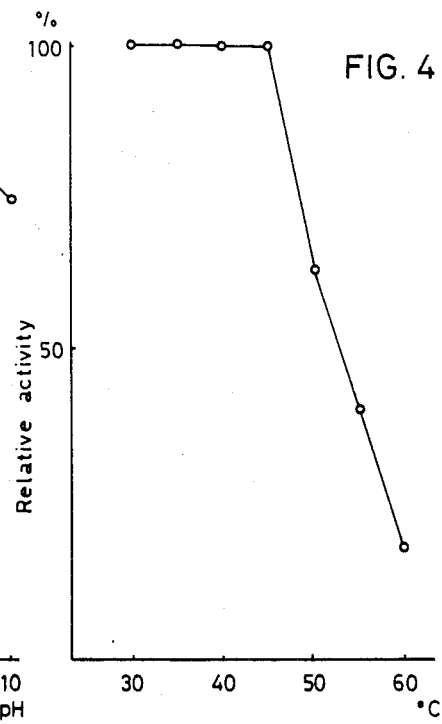
FIG. 4 shows a relation between the temperature and activity after treating bilirubin oxidase at a pH of 6.0 and at varying temperatures for 10 minutes.

An optimum temperature for the present enzyme is about 50° C. as shown by the curve in FIG. 2. The thermostability of the present enzyme when it was treated at a pH of 6.0 and at varying temperatures for 10 minutes, is shown in FIG. 4. The present enzyme was stable up to 45° C.

(4) Molecular weight

The molecular weight of the present enzyme obtained by gel filtration with Sephadex G-100 was about 58,000.

(5) Isoelectric point

The isoelectric point of the present enzyme obtained by isoelectric focusing was 6.0 to 6.1.

(6) Inhibitor

The present enzyme was inhibited by 1 mM each of Fe$^{2+}$, NaN$_3$, KCN, sodium ascorbate, Cu$^{2+}$, o-phenanthroline, α,α'-dipyridyl, reduced glutathione and the like.

(7) Determination of enzymatic activity

The enzymatic activity was obtained by measuring a decrease in the absorption of bilirubin at 460 nm. That is, reaction was carried out at 37° C. for 10 minutes using 3.0 ml of a reaction mixture containing 8 mg of OMEGA-chemistry Control Serum Elevated Bilirubin (produced by Hyland Co., U.S.A.), 300 μmoles of phosphate buffer (pH, 6.0) and 0.1 ml of properly diluted enzyme solution, and a decrease in absorption at 460 nm due to bilirubin was measured. One unit of bilirubin oxidase activity was defined as the amount of the enzyme which decreases the absorption at 460 nm by 1.00 per minute at 37° C.

The concrete method for producing bilirubin oxidase according to the present invention will be illustrated with reference to the following examples, which are not however to be interpreted as limiting the invention thereto.

EXAMPLE 1

A slant culture medium comprising 2% of glucose, 0.5% of Ebios and 1.5% of agar (Ebios medium) was inoculated with *Schizophyllum commune* K-17 (FERM BP-306), and cultivation was carried out by keeping the medium still at 25° C. for one week to obtain a seed fungus. Separately from this, 100 ml of a culture medium comprising 3% of glycerol, 0.3% of yeast extract, 1% of peptone, 0.3% of KH$_2$PO$_4$ and 0.1% of MgSO$_4$.7H$_2$O was added to a 500-ml Erlenmeyer flask, and after being sterilized at 120° C. for 20 minutes, it was cooled and inoculated with the above seed fungus. Thereafter, shaking culture was carried out at 27° C. for 7 days at 120 revolutions per minute. After completion of the culture, the mycelium was removed by filtration to obtain a culture filtrate. The bilirubin oxidase activity of this culture filtrate was 1.5 units/ml.

EXAMPLE 2

One hundred milliliters of a culture medium comprising 3% of glycerol, 0.3% of yeast extract, 1% of peptone, 0.3% of KH$_2$PO$_4$ and 0.1% of MgSO$_4$.7H$_2$O was added to a 500-ml Erlenmeyer flask, sterilized at 120° C. for 20 minutes and inoculated with *Schizophyllum commune* K-17 cultivated in the Ebios culture medium of Example 1. Thereafter, cultivation was carried out at 27° C. for 5 days to prepare a seed culture liquor. Separately from this, 15 liters of a culture medium comprising 3% of glycerol, 0.3% of yeast extract, 0.5% of peptone, 1% of corn steep liquor, 1% of defatted soybean, 0.3% of KH$_2$PO$_4$, 0.1% of MgSO$_4$.7H$_2$O and 0.03% of a defoaming agent (CB-442 produced by Nippon Yushi Co.) was added to a 30-liter jar fermenter, and sterilized at 120° C. for 20 minutes. After cooling, the culture medium was inoculated with 100 ml of the above seed culture liquor, and cultivation was carried out at 27° C. for 6 days at an aeration rate of 10 liters per minute and stirring rate of 200 revolutions per minute. After completion of the cultivation, the mycelium was removed by filtration to obtain a culture filtrate. The bilirubin oxidase activity of this culture filtrate was 6.5 units/ml. Ammonium sulfate was added to 13 liters of this culture filtrate at first until 50% saturation to remove impurities as precipitate. Ammonium sulfate was further added to the supernatant liquor until 70% saturation, and after allowing to stand for a whole day and night, the resulting ammonium sulfate precipitate was dialyzed for a whole day and night against a large quantity of distilled water. The internal solution of dialysis was lyophilized, and the dry powder obtained was dissolved in 0.1M phosphate buffer (pH, 7.0). Gel filtration of the resulting solution was carried out on a column (5.0×70 cm) of Sephadex G-75 buffered with the same buffer to collect an active fraction. The active fraction was adsorbed to a column (5.0×20 cm) of DEAE-Sephadex A-50 previously buffered with 0.1M phosphate buffer (pH, 7.0), and the adsorbed matter was eluted with 0.3M phosphate buffer (pH, 7.0). This active fraction was dialyzed against 0.01M phosphate buffer (pH, 7.0), and the internal solution of dialysis was concentrated with a collodion membrane and lyophilized to obtain 320 mg of the purified enzyme powder. The specific activity of this powder was 23 units/mg.

In the reaction of this purified enzyme with OMEGA-chemistry Control Serum Elevated Bilirubin, a relation between the reaction time (amount of purified enzyme used, 0.2 μg) and the enzyme concentration (reaction time, 10 minutes) affecting a decrease in absorption at 460 nm due to bilirubin (ΔA460 nm) was studied.

| Reaction time (min.) | ΔA460 nm | Enzyme concentration (μg) | ΔA460 nm |
| --- | --- | --- | --- |
| 10 | 0.048 | 0.2 | 0.047 |
| 20 | 0.093 | 0.4 | 0.0912 |
| 30 | 0.135 | 0.6 | 0.135 |
| 40 | 0.168 | 0.8 | 0.170 |

As shown above, the purified enzyme has a property to decrease bilirubin when it is reacted with bilirubin.

Figure 5:
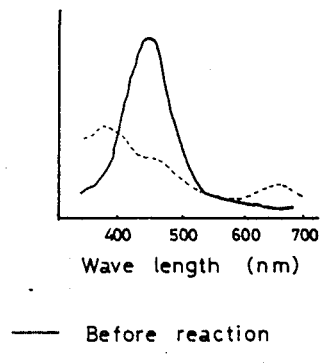
FIG. 5 shows a change in absorption spectrum when the present enzyme was reacted with OMEGA-chemistry Control Serum Elevated Bilirubin.
Figure 6:
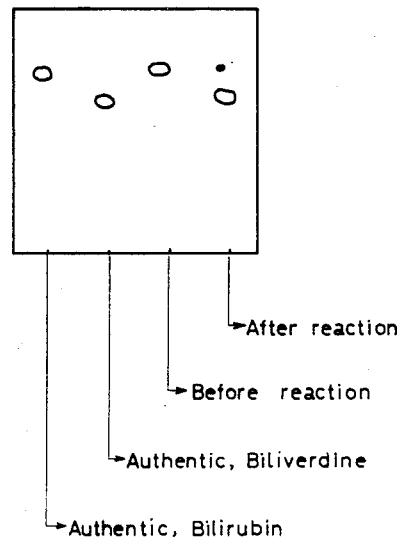
FIG. 6 shows the thin layer chromatogram of the reaction product obtained when the present enzyme was reacted with OMEGA-chemistry Control Serum Elevated Bilirubin.
Figure 7:
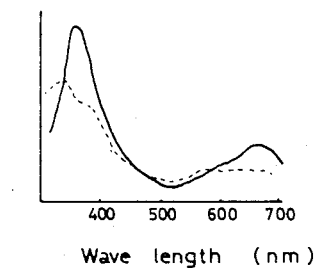
FIG. 7 shows a change in absorption spectrum when the present enzyme was reacted with biliverdine.

Next, from the result of absorption spectrum (FIG. 5) when the purified enzyme was reacted with OMEGA-chemistry Control Serum Elevated Bilirubin, as well as the result of thin layer chromatography (FIG. 6) with a chloroform/methanol (1:1) mixed solvent, the formation of an oxidized product of bilirubin, i.e. biliverdine, was observed. Consequently, it was found that the present enzyme is bilirubin oxidase which will oxidize bilirubin to biliverdine. Also, the present enzyme had a property to oxidize biliverdine to an unknown pale violet substance (absorption spectrum is shown in FIG. 7).

What we claim is:

1. A method for producing bilirubin oxidase which comprises cultivating *Schizophyllum commune* K-17 (FERM BP-306) in a culture medium, and collecting bilirubin oxidase from the resulting culture broth.

* * * * *